United States Patent [19]

Peyman et al.

[11] Patent Number: 4,674,503
[45] Date of Patent: Jun. 23, 1987

[54] CONTROLLED DEPTH PENETRANT APPARATUS AND METHOD

[76] Inventors: Gholam A. Peyman, 535 N. Michigan Ave., Chicago, Ill. 60611; James M. Grisolano, Jr., Rte. 2, Box 166H, Baxter, Tenn. 38544

[21] Appl. No.: 240,728

[22] Filed: Mar. 5, 1981

[51] Int. Cl.[4] .............................................. A61B 17/32
[52] U.S. Cl. ...................................... 128/305; 83/881
[58] Field of Search ................ 128/305, 305.1, 329 R, 128/305.5; 83/881

[56] References Cited

U.S. PATENT DOCUMENTS

| | | | |
|---|---|---|---|
| 2,328,244 | 8/1943 | Woodward | 143/41 |
| 2,565,727 | 8/1951 | Henderson | 17/4 |
| 3,076,365 | 2/1963 | Taylor et al. | 83/63 |
| 3,476,112 | 11/1969 | Elstein | 128/305 |
| 3,555,950 | 1/1971 | Glusbers | 83/171 |
| 3,670,733 | 6/1972 | Carlisle | 128/305 |
| 3,756,104 | 9/1973 | Bier et al. | 83/8 |
| 3,848,490 | 11/1974 | Arel | 83/49 |
| 3,945,279 | 3/1976 | Boehme | 83/34 |
| 4,026,295 | 5/1977 | Lieberman | 128/305 |
| 4,154,228 | 5/1979 | Feldstein et al. | 128/329 R |
| 4,180,075 | 12/1979 | Marinoff | 128/305 |
| 4,205,682 | 6/1980 | Crock et al. | 128/305 |
| 4,269,192 | 5/1981 | Matsuo | 128/329 R X |
| 4,299,230 | 11/1981 | Kubota | 128/329 R X |
| 4,546,773 | 10/1985 | Kremer et al. | 128/660 |

OTHER PUBLICATIONS

Schachar et al, "Radial Keratotomy", Chapter XXIII, pp. 201-212 (1980).

Primary Examiner—Michael H. Thaler
Attorney, Agent, or Firm—Thomas A. Kmiotek

[57] ABSTRACT

A penetrant apparatus for controlling the depth that a penetrant device penetrates a material relative to its outer surface, where the cross-sectional thickness of the material is not susceptible to caliper-type measurement because its inner surface is inaccessible except by intrusive means, and a method for penetrating the material utilizing the apparatus. The apparatus comprises a penetrant device connected to and driven by driving apparatus, depth sensing apparatus, thickness sensing apparatus, and comparator apparatus. The depth sensing apparatus determines the depth of penetration of the penetrant device into the material while the thickness sensing apparatus determines the thickness of the material between its inner and outer surfaces. The comparator apparatus is connected to the depth sensing apparatus, the thickness sensing apparatus, and the driving apparatus and compares the depth of penetration of the penetrant device to the thickness of the material and control the driving apparatus so that the depth of penetration of the penetrant device relative to the material's outer surface so as to leave unpenetrated a portion of the material adjacent the inner surface.

34 Claims, 8 Drawing Figures

CONTROLLED DEPTH PENETRANT APPARATUS AND METHOD

BACKGROUND OF THE INVENTION

1. Field of the Invention

This invention relates generally to penetrant devices. It particularly relates to a penetrant apparatus and method for controlling the depth that a penetrant means penetrates a material relative to its outer surface, where the cross-sectional thickness of the material is not susceptible to caliper-type measurement because its inner surface is inaccessible except by intrusive means.

2. Background of the Invention

When a procedure requires the penetration of a material to a precise depth, resort to the use of a guarded instrument is typical. In such an instrument its depth of penetration into a material is governed by the placement of a shoulder stop, which prevents further penetration of the instrument. Certain machining procedures use shoulder-stops, namely drilling operations into material stock where partial depth holes are drilled. Material removal operations on multilayer plates utilize cutting devices in combination with depth-of-cut restriction devices. Operators or technicians may also rely on acquired skill without the aid of guarded instruments or depth-of-cut restriction devices for drilling partial depth holes or for material removal operations on multilayer plates.

These methods are usually satisfactory if penetration of the material to only an approximate desired depth is required and variation in thickness of the material is not critical. However, where penetration of a material to a precise depth is critical, or where a material removal operation or cutting procedure is microscopic in nature, inherently requiring precise depth penetration with tolerences on the order of several microns, the aforesaid techniques known to the art are crude and oftentimes of unacceptable riskiness. In general material removal operations the risk is in terms of lost material and lost time.

Cutting tools and penetrant apparatus in common use cannot be used for penetrating a material whose inner surface is inaccessible, except by intrusive means, where the unpenetrated thickness of material at any point adjacent the material's inner surface is required to be precisely controlled, or to comprise a uniform proportional thickness of the material at that point. This is especially the case when the cross section of the portion of material to be penetrated is neither a constant thickness nor uniformly varying in thickness. The known guarded instruments with shoulder stops would have to be continuously adjusted as the penetrant means or cutting tool traverses the outer surface of the material, which could only be done if the thickness of the material at the point of penetration were also known. Yet, if the inner surface is inaccessible, the necessary thickness measurements are impossible, rendering use of such instruments impractical if not prohibited.

The difficulties encountered in the use of general cutting tools and penetrant apparatus just discussed become particularly acute in surgical procedures where safety and efficacy are major concerns and where any risk can be unacceptable. Surgical procedures often utilize surgical instruments of construction identical to those known in the art for penetrating of materials generally. Guarded surgical instruments use shoulder stops when penetration of a material or tissue to a certain depth is required.

Oftentimes surgical procedures require the penetration of a material or tissue in such a manner that a portion of the cross-sectional thickness of the material or tissue is left unpenetrated adjacent its inner surface, that unpenetrated portion being of a precise thickness or a uniform proportion of the thickness of the material at the point of penetration. That is, it is not uncommon for a surgical procedure to define the depth of penetration of a penetrant means with respect to a reference inner surface.

Typically, though, the material or tissue having a defined outer surface and inner surface is not susceptible to a caliper-type measurement because the inner surface is inaccessible except by intrusive means. Also, for any given portion of material or tissue, the cross-sectional thickness is often not constant and ordinarily varies in a nonuniform manner.

Variation in the cross-sectional thickness of a material is not a critical factor when the penetration of the material or tissue involves the insertion of a needle or a probe so as to leave unpenetrated a precise thickness or a uniform proportion of the thickness of the material at the point of penetration. The insertion of a needle or probe in the situation just described, however, requires the simultaneous thickness measurement of the material or tissue and the measurement of the depth of penetration of the needle or probe at the point of penetration Variation of the cross-sectional thickness of a material becomes a factor when the penetration effected is an incision. With an incision, not only must the thickness measurement of the material or tissue be simultaneous with the measurement of the depth of penetration of the penetrant means, but, as the cutting blade linearly incises the material or tissue while traversing the outer surface, the measurements continuously change, requiring a corresponding adjustment in depth of cut.

Another factor must be considered in the insertion of a needle or probe, as well as in a cutting blade incision. When the material or tissue is penetrated by a needle, probe or cutting blade, the material or tissue deforms at the point of penetration. Control of the penetration of the penetrant means must account for this deformation. Simultaneous measurement of the thickness of the material or tissue and measurement of the depth of penetration must also take into account this deformation of the material or tissue.

Ultrasound machines in common use can be used to measure the thickness between the outer surface of a material or tissue and a reference inner surface. Their current usefulness is limited, however, to a thickness measurement just prior to manual insertion of a needle or probe. Once the thickness between the outer surface and the reference inner surface of a material has been determined, the needle or probe is inserted at approximately the point of thickness measurement. A length of needle or probe corresponding to the desired depth of penetration is physically measured on the needle or probe using a scaled rule. Penetration beyond the measured point is usually limited by a shoulder stop. The disadvantage to this type of measurement is that the tolerances are only on the order of approximately one sixteenth of an inch; tolerances on the order of a few microns are impossible.

Skillful surgical technique is still the most efficacious procedure in the insertion of a needle or probe, or in making an incision with a cutting blade. But again, even skillful surgeons cannot consistently incise a material or tissue leaving an unpenetrated thickness of uniform or uniform proportional thickness of the material or tissue adjacent an inner surface. Indeed, when surgery is microscopic in nature, incisions to a precise depth relative to an outer surface are extremely difficult. The surgical difficulty is increased in microfine work when the unpenetrated portion of material adjacent to the inner surface must be of substantially uniform thickness or where the unpenetrated portion of material at any point adjacent to the inner surface must be a substantially uniform proportion of the material at said point.

The lack of apparatus and methods in the art affording precise and controlled placement or penetration of a penetrant means together with the combined continuous functions of thickness measurement and measurement of the depth of penetration of the penetrant means are particularly critical in surgical procedures such as radial keratotomy, amniocentesis, venous puncture, arterial puncture, aspiration of a cyst, or spinal taps.

Radial keratotomy is a new surgical procedure for correction of refractive errors in the eye of an animal, particularly humans. The procedure involves penetrating the cornea inwardly from its outer surface with a cutting blade while leaving adjacent to its inner surface an unpenetrated portion of corneal tissue. A plurality of partial thickness radial incisions of precise depth are made which traverse the cornea and which radiate from the anterior pole to the limbus. The incisions are made as deeply as possible with respect to the inner surface of the cornea (Decemet's membrane or the endothelium) without piercing it. If the knife penetrates into the anterior chamber of the eye, infection (endophthalmitis) may result. Insufficient penetration prevents surgical correction of the refractive error. Presently the depth of corneal incision is monitored by microscopic direct vision when using either guarded or unguarded cutting blades. The most successful results in the correction of refractive error occur if the thickness of cornea left uncut is a uniform number of microns from the inner surface of the cornea or a uniform proportional thickness of the original thickness.

The procedure is simple in terms of the surgical details, but is technically difficult because the average cornea is only about 500 microns thick at the anterior pole, and varies in thickness radially from the anterior pole in a nonuniform manner. In addition, the unsteadiness of even a skilled surgeon's hand at this microscopic level risks penetration into the anterior chamber of the eye and later resulting endophthalmitis.

The art does not provide a surgical instrument or method where the thickness of the cornea is continuously monitored while continuously monitoring the depth of penetration of the cutting blade in order to automatically maintain the cutting blade at the proper position from the inner surface of the cornea to within tolerances of a few microns while the traversing incisions are made.

In amniocentesis, embryonic fluid is removed from inside the womb by using a needle. Penetration of the needle to a precise depth is critical; if the needle penetrates too deeply into the womb, there is a risk of injury to the fetus.

The art does not provide a surgical instrument or method where the position of the fetus (as an reference inner surface) is discriminated and fetal position is continuously monitored while a needle is inserted into the womb to a precise distance from the fetus and while the position of the needle tip is also continuously monitored.

In venous puncture, arterial puncture, or aspiration of a cyst, a needle penetrates the near wall of a vein or artery, or the near surface of a cyst, and is further inserted so that the needle tip is fully inside the vein, artery or cyst. Further penetration is halted so that the needle does not pierce the far wall of the vein, artery or cyst. The present method of manual insertion risks the possibility of penetrating the far wall or surface. Also, if manual insertion is done too slowly the vein, artery or cyst may be displaced to one side or the walls of the vein, artery or cyst may become invaginated.

The art does not provide a surgical instrument or method for performing a venous or arterial puncture, or aspiration of a cyst, where the far wall or surface is used as the reference inner surface and the needle is inserted to a precise depth from the reference inner surface while the position of the reference inner surface and the position of the needle tip are continuously monitored.

Spinal taps require the precise placement of a needle into the spinal cord. Once penetration of the near wall of the spinal cord has been achieved, the needle is further inserted but is eventually stopped short of penetration of the far wall. The present methods of manual insertion risk the penetration of the far wall. This would require manual adjustments in the depth of needle penetration or another attempt at the spinal tap.

The art does not provide a surgical instrument or method for continuously monitoring the position of the far wall of the spinal cord in order to determine the thickness of material between the skin surface and far wall while continuously monitoring and controlling the position of the needle during insertion.

As can be appreciated by considering the aforesaid material penetration methods and the aforesaid surgical procedures, it is apparent that none of the apparatus or methods known to the art control the penetration of a material having an outer surface and a substantially inaccessible inner surface by continuously monitoring thickness and depth of penetration of the penetrant means while adjusting the depth of penetration, such that the unpenetrated portion of material adjacent to the inner surface is of substantially uniform thickness, or such that the unpenetrated portion of material at any point adjacent to the inner surface is a substantially uniform proportion of the material at said point.

As a result, there is a need in the art for a cutting tool or penetrant apparatus for penetrating a material having an outer surface and an inner surface whose inner surface is inaccessible (except by intrusive means), which apparatus adjusts the penetration of the penetrant means so that the unpenetrated portion of the material at a point adjacent to the inner surface is of substantially uniform thickness or is a substantially uniform proportion of the thickness of the material at said point. The cutting tool or penetrant apparatus would be able to cut or penetrate a material and leave a desired portion of material uncut or unpenetrated adjacent the material's inner surface both when the cross section of the portion of material to be penetrated was non-constant in thickness and when it did not vary uniformly in thickness. Furthermore, the penetrant means or cutting tool would be continuously adjusted to accommodate the varying cross-sectional thickness of the material as the cutting tool or penetrant apparatus traversed its outer surface, so that the unpenetrated portion at any point adjacent the material's inner surface would be the desired uniform thickness or the desired uniform proportional thickness of the material at that point of penetration.

Similarly, there is a need in the art for a surgical instrument for penetrating a material or tissue having an outer surface and an inner surface whose inner surface is inaccessible (except by intrusive means), which apparatus adjusts the penetration of the penetrant means so that the unpenetrated portion of the material or tissue at a point adjacent to the inner surface is of substantially uniform thickness or is a substantially uniform proportion of the thickness of the material or tissue at said point. The surgical instrument would be capable of use in microscopic surgery where penetration to a precise depth is required, as well as where the unpenetrated portion of the material or tissue at a point adjacent to the inner surface must be a substantially uniform thickness or a substantially uniform proportion of the thickness of the material or tissue at the point of penetration. Precise and controlled penetration of a penetrant means would be combined with the continuous functions of thickness measurement and measurement of the depth of penetration of the penetrant means.

More specifically, there is a need in the art for a surgical instrument for performing a radial keratotomy where the thickness of the cornea is continuously monitored and, simultaneously, the depth of penetration of the cutting blade is continuously monitored and adjusted, so that the cutting blade would be maintained at the proper position from the inner surface of the cornea to within tolerances of a few microns.

A surgical instrument for amniocentesis is also needed which would disclose and continuously monitor fetal position while controlling the insertion of a needle into the womb to a precise distance from the fetus and while continuously monitoring the position of the needle tip.

A similar demand for a surgical instrument for performing venous puncture, arterial puncture, or aspiration of a cyst which would automatically insert a needle to a precise distance from the far walls of a vein, artery or cyst (inner surfaces) also exists in the art. The insertion of the needle would be quick enough to minimize displacement of the vein, artery or cyst and to minimize the chances of invaginating the walls of the vein, artery or cyst. The position of the reference inner surface and the position of the needle tip would be continuously monitored so that adjustment of the penetration would be continuously controlled.

Finally, a requirement exists for a surgical instrument for performing spinal taps which would automatically insert a needle to a precise distance from the far wall of the spinal cord (inner surface). The position of the inner surface and the position of the needle tip would be continuously monitored so that adjustment of the penetration would be continuously controlled.

SUMMARY OF THE INVENTION

The present invention relates to an apparatus for and a method of penetrating a material which has an outer surface and an inaccessible inner surface, which apparatus and method satisfy the aforestated lackings and needs in the art by utilizing penetrant means whereby the penetration of said penetrant means is adjusted such that there remains unpenetrated a portion of material at a point adjacent to the inner surface that is a substantially uniform thickness or a substantially uniform proportion of the thickness of the material at said point.

The apparatus comprises penetrant means which penetrate the material and which are connected to and driven by driving means which adjust the depth of penetration of the penetrant means relative to the outer surface of the material. Additional elements of the apparatus comprise depth sensing means, thickness sensing means, and comparator means. The depth sensing means determine the depth of penetration of the penetrant means into the material relative to the outer surface. Simultaneously, and at substantially if not literally the point of penetration of the penetrant means, the thickness sensing means determine the thickness of the material between the outer surface and the inner surface.

The comparator means are connected to the depth sensing means, thickness sensing means, and driving means. An operator inputs a signal proportional to the unpenetrated thickness to remain adjacent to the inner surface of said material. Once the depth sensing means determine the depth of penetration of the penetrant means, a signal proportional thereto is provided by said means to the comparator means. Likewise, once the thickness sensing means determine the thickness of the material a signal proportional thereto is also provided by said means to the comparator means. The comparator means compare the depth of penetration of the penetrant means to the input of the desired unpenetrated thickness adjacent to the inner surface and to the thickness of the material. The comparator means then control the driving means so that the penetrant means leave unpenetrated the desired unpenetrated thickness adjacent to the inner surface.

More particularly, a surgical instrument is provided for performing a radial keratotomy, in which procedure the material penetrated is the cornea of the eye of an animal. A cutting blade is the penetrant means, which blade incises the cornea as the instrument traverses the outer surface of the cornea.

The method of this invention relates to penetrating a material which has an outer surface and an inaccessible inner surface by utilizing penetrant means whereby the penetration of said penetrant means is adjusted such that there remains unpenetrated a portion of material at a point adjacent to the inner surface that is a substantially uniform thickness or a substantially uniform proportion of the thickness of the material at said point.

The method comprises continuously measuring the thickness of the material between the outer surface and the inner surface at substantially if not literally the point of intended penetration of the penetrant means by utilizing thickness sensing means. The method thereafter comprises penetrating the material with the penetrant means and controlling the penetration of the penetrant means relative to the outer surface of the material by driving means connected to said penetrant means. While the material is being penetrated the depth of penetration of the penetrant means relative to the outer surface of the material is continuously measured by depth sensing means. The depth of penetration of the penetrant means is then compared, by comparator means, to the desired unpenetrated thickness adjacent to the inner surface and to the thickness of the material at substantially the point of penetration of the penetrant means. Adjustment of the depth of penetration of the penetrant means is controlled by the comparator means so that the desired unpenetrated thickness adjacent to the inner surface is left unpenetrated.

When the penetrant means traverse the outer surface of the material, continuous adjustment of the penetrant means is effected by advancing or retracting said penetrant means so that the desired unpenetrated thickness adjacent to the inner surface is left unpenetrated.

More particularly, the method of the invention comprises a surgical method for performing a radial keratotomy, in which procedure the material penetrated is the cornea of the eye of an animal. Penetration is effected by a cutting blade that incises the cornea as the instrument traverses the outer surface of the cornea.

The present invention overcomes the drawbacks of the prior art by providing the abovementioned apparatus and method for controlling the depth of penetration that a penetrant means penetrates the outer surface of a material whose inner surface is substantially inaccessible. Simultaneous with the penetration the thickness of the material from the outer surface to the inaccessible inner surface is measured by the thickness sensing means of the apparatus and the depth of penetration of the penetrant means is measured by the depth sensing means of the apparatus. The depth of penetration is compared, by the comparator means of the apparatus, to the desired unpenetrated thickness adjacent to the inner surface and to the thickness of the material at substantially the point of penetration of the penetrant means. The comparator means then control the adjustment of penetration so that the movement of the penetrant means inwardly or outwardly with respect to the outer surface of the material is adjusted so as to leave unpenetrated the desired portion of the material adjacent the inner surface.

Accordingly, it is an object of this invention to provide a cutting tool or penetrant apparatus for penetrating a material having an outer surface and an inner surface which is inaccessible (except by intrusive means), which apparatus penetrates the outer surface of said material while leaving unpenetrated adjacent the material's inner surface a uniform thickness or a uniform proportional thickness of the material at the point of penetration, where the cross section of the portion of material penetrated is neither a constant thickness nor uniformly varying in thickness, by continuously adjusting the depth of penetration of the penetrant means to accommodate for the varying cross sectional thickness as the cutting tool or penetrant apparatus traverses the outer surface of the material.

It is another object of this invention to provide a surgical instrument for penetrating a material or tissue having an outer surface and an inner surface which is inaccessible (except by intrusive means), which instrument penetrates the outer surface of said material or tissue while leaving unpenetrated adjacent the material's or tissue's inner surface a uniform thickness or a uniform proportional thickness of the material or tissue at the point of penetration, and is of sufficiently high accuracy to be adaptable to microfine surgery.

It is still another object of this invention to provide a surgical instrument for performing a radial keratotomy where the thickness of the cornea is continuously monitored; simultaneously, the depth of penetration of a cutting blade is continuously monitored and adjusted so that the cutting blade is maintained at a position leaving unpenetrated adjacent the corneal inner surface at any point a uniform thickness or a uniform proportional thickness of cornea at the point of penetration.

It is a further object of this invention to provide a surgical instrument for amniocentesis which discloses and continuously monitors fetal position while controlling the insertion of a needle into the womb to a precise distance from the fetus while continuously monitoring the position of the needle tip.

It is yet another object of this invention to provide a surgical instrument for performing venous puncture, arterial puncture, or aspiration of a cyst which instrument inserts a needle to a precise distance from the far walls of a vein, artery or cyst (inner surfaces), said insertion being quick enough to minimize displacement of the vein, artery or cyst and to minimize the chances of invaginating the walls of the vein, artery, or cyst, and by which the position of said needle tip is continuously monitored and adjustment of the insertion is continuously controlled.

Finally, it is another object of this invention to provide a surgical instrument for performing spinal taps which instrument inserts a needle to a precise distance from the far wall of the spinal cord (inner surface) by continuously monitoring the position of the inner surface and the position of the needle tip and continuously controlling adjustment of the needle insertion.

Other objects and advantages of this invention will become apparent upon reading the following detailed description and appended claims, and upon reference to the accompanying drawings.

BRIEF DESCRIPTION OF THE DRAWINGS

For a more complete understanding of this invention reference should now be had to the several embodiments illustrated in greater detail in the accompanying drawings.

In the drawings.

DESCRIPTION OF THE PREFERRED EMBODIMENTS

The preferred embodiments of this invention provide an apparatus powered by an external electrical power supply for penetrating a material which has an outer surface and an inner surface, whereby said material is penetrated inwardly from said outer surface while leaving adjacent to said inner surface an unpenetrated portion thereof. The apparatus preferably comprises penetrant means for penetrating the material to which driving means are connected for advancing or retracting said penetrant means relative to the outer surface of the material. The apparatus further comprises depth sensing means, thickness sensing means and comparator means. The depth sensing means determine the depth of penetration of said penetrant means into the material relative to the outer surface of the material and generate a signal proportional to the depth of penetration. The thickness sensing means determine the thickness of the material between the outer and inner surfaces of the material at a point directly adjacent thereto, said point also being substantially the point of penetration of said penetrant means. The thickness sensing means thereafter generate a signal proportional to said thickness.

The comparator means are connected to said depth sensing means, thickness sensing means, and driving means. The comparator means compare the signal proportional to the depth of penetration of said penetrant means into the material relative to the material's outer surface, generated by the depth sensing means, to an input signal proportional to the desired unpenetrated thickness adjacent to the inner surface of the material and to the signal proportional to the thickness of the material at substantially the point of penetration of said penetrant means, generated by the thickness sensing means. Thereafter, said comparator means provide an output signal which controls said driving means so that the penetration of said penetrant means inwardly or outwardly with respect to the outer surface of the material is adjusted, thereby leaving unpenetrated a portion of the material adjacent the inner surface.

The output signal provided by said comparator means in the preferred embodiment of the invention, which thereby controls said driving means, is such that the penetration of said penetrant means leaves unpenetrated at any point adjacent the inner surface a portion of the material which is either substantially uniform in thickness or a substantially uniform proportion of the thickness of the material at that point.

Particularly preferred penetrant means for penetrating the material are a cutting blade, a needle, and a probe. Particularly preferred driving means connected to said penetrant means for advancing or retracting said penetrant means comprise an electric motor, gear train and transmission arrangement which convert the rotational motion of the motor to the desired linear motion of said penetrant means. An alternative embodiment for said driving means can also comprise hydraulic direct drive means.

Preferred embodiments for the depth sensing means for determination of the depth of penetration of said penetrant means relative to the outer surface of the material include a photocell micrometer, ultrasound transducer means, and a variable resistor vernier. A particularly preferred embodiment for said depth sensing means is ultrasound transducer means. The most preferred embodiment for said depth sensing means is a photocell micrometer.

The variable resistor vernier embodiment of said depth sensing means comprises a resistor fixed to a penetrant means holder frame and a slidable penetrant means holder having an electrical contact attached thereto for contacting the resistor. As said penetrant means advance or retract relative to the outer surface of the material, the slidable penetrant means holder changes position relative to the fixed penetrant means holder frame and the fixed resistor. The measured electrical potential between a fixed position on the resistor and a point of electrical contact on the resistor corresponding to the position of the slidable penetrant means holder comprises an output signal representative of the depth of penetration of said penetrant means. The variable resistor vernier output signal is thereafter provided to said comparator means.

The ultrasound transducer means embodiment of said depth sensing means comprises an ultrasound transducer unit which generates and receives ultrasound measuring signals, which transducer unit is coupled to an ultrasound transducer probe. The generated ultrasound measuring signal is inwardly directed with respect to the outer surface of the material. Thereafter, said transducer means receive a plurality of reflected signals, including the signal from the outer surface of the material, those from surfaces beneath the outer surface of the material, and those from the penetrant means. A tone generator connected to said transducer means generates an audio frequency which frequency increases corresponding to greater deviation of the measuring signal from perpendicular orientation, and decreases corresponding to less deviation from perpendicular orientation, allowing manual adjustment of the position of the transducer probe to a perpendicular orientation to the surface to be penetrated to be effected by noting the audio frequency generated.

For the most accurate determination of penetrant means depth, the ultrasound transducer probe should be within approximately 10 degrees of perpendicular orientation to the material's outer surface tangent at the point that the penetrant means depth is to be determined. Deviation from perpendicular orientation of the ultrasound transducer probe directs the ultrasound measuring signal, and correspondingly the reflected signals, through a greater thickness of material, resulting in parallax, viz., misperception of distances between the underlying surfaces and between the penetrant means tip and the outer surface of the material.

From among the plurality of reflected signals received by said ultrasound transducer means, discriminating means incorporated into said ultrasound transducer unit are utilized to select those signals representing the material's outer surface reflection and the penetrant means tip reflection. The ultrasound transducer means thereafter generate an output signal from the selected material outer surface and penetrant means tip reflection signals, which signal is representative of the depth of penetration of said penetrant means. The ultrasound transducer means output signal is thereafter provided to said comparator means.

Preferred embodiments for the thickness sensing means for determination of the thickness of the material are ultrasound transducer means and light transducer means. A particularly preferred embodiment for said thickness sensing means comprise an ultrasound transducer means.

The ultrasound transducer means embodiment of said thickness sensing means comprises an ultrasound transducer unit which generates and receives ultrasound measuring signals, which transducer unit is coupled to an ultrasound transducer probe. The generated ultrasound measuring signal is inwardly directed with respect to the outer surface of the material. Thereafter, said transducer means receive a plurality of reflected signals, including the signal from the outer surface of the material and those from surfaces beneath the outer surface of the material. A tone generator connected to said transducer unit generates an audio frequency which frequency increases corresponding to greater deviation of the measuring signal from perpendicular orientation, and which decreases corresponding to less deviation from perpendicular orientation, allowing manual adjustment of the position of the transducer probe to a perpendicular orientation to the surface to be penetrated to be effected by noting the audio frequency generated.

For the most accurate determination of material thickness the ultrasound transducer probe should be within approximately 10 degrees of perpendicular orientation to the material's outer surface tangent at the point that the material thickness is to be determined. Deviation from perpendicular orientation of the ultrasound transducer probe directs the ultrasound measuring signal, and correspondingly the reflected signals, through a greater thickness of material resulting in parallax, viz., misperception of distances between the underlying surfaces.

From among the plurality of reflected signals received by said ultrasound transducer means, discriminating means incorporated into said ultrasound transducer unit are utilized to select from the signals, those representing the material inner and outer surface reflections. The ultrasound transducer means thereafter generate an output signal from the selected material reflection signals, which signal is representative of the thickness of the material. The ultrasound transducer means' output signal is thereafter provided to said comparator means.

The light transducer means embodiment for said thickness sensing means comprise a light transducer unit and a light transducer probe. The thickness of the material between the inner and outer surfaces of the material is determined by said light transducer unit coupled to said light transducer probe, generating and receiving a plurality of measuring polarized light signals. The generated measuring polarized light signals are inwardly directed with respect to the outer surface of the material. The transducer probe itself is substantially perpendicular to the surface of the material while the angle of incidence of the plurality of polarized light signals generated from the transducer probe and inwardly directed is an angle other than 90 degrees. Thereafter, said transducer probe receives a plurality of reflected light signals from an inner surface beneath the outer surface of the material. The plurality of signals reflected from the material inner surface are received by the light transducer probe at a measurable distance from the point where said light signals were generated, said distance being directly proportional to the thickness of the material. The transducer probe which receives said plurality of reflected light signals at said measurable distance from the point where said light signals were generated thereafter generates an intermediate signal which is representative of both said distance and the perpendicular orientation of the transducer probe with respect to the surface to be penetrated and passes said intermediate signal to the light transducer unit.

A tone generator connected to said transducer unit generates an audio frequency which increases corresponding to greater deviation of the transducer probe from perpendicular orientation, and which decreases corresponding to less deviation from perpendicular orientation allowing manual adjustment of the position of the transducer probe to a perpendicular orientation to the surface to be penetrated to be effected by noting the audio frequency generated. For the most accurate determination of material thickness the transducer probe should be within approximately 10 degrees of perpendicular orientation to the material's outer surface tangent at the point that the material thickness is to be determined. Deviation from perpendicular orientation of the transducer probe directs the polarized light measuring signals, and correspondingly the reflected light signals, through a greater thickness of material resulting in parallax, viz., misperception of distances between the underlying surfaces and the outer surface of the material.

From the signal received by said light transducer unit, the light transducer unit thereafter computes and generates an output signal from the intermediate signal, which signal is representative of the thickness of the material. The light transducer means' output signal thereafter is passed to said comparator means.

A particularly preferred embodiment of this invention provides for ultrasound transducer means comprising both said thickness sensing means and said depth sensing means. In this embodiment the thickness of the material between the outer and inner surfaces thereof and the depth of penetration of said penetrant means into said material relative to the outer surface are determined by said transducer means comprising an ultrasound transducer unit which generates and receives ultrasound measuring signals, which transducer unit is coupled to an ultrasound transducer probe. The measuring signal is inwardly directed with respect to the outer surface of the material. Thereafter, said transducer unit receives a plurality of reflected signals including the signal from the outer surface of the material, those from surfaces beneath the outer surface of the material, and those from the penetrant means. As earlier described in the discussion of a preferred embodiment of thickness sensing means comprising an ultrasound transducer means, a tone generator connected to said transducer means indicates the perpendicular orientation of the probe and therefore the measuring signal so that manual adjustment to perpendicular orientation can be effected.

From among the plurality of reflected signals received by said transducer means, discriminating means incorporated into said ultrasound transducer unit are utilized to select from said signals those representing the material inner and outer surface reflections and the penetrant means tip reflection. The ultrasound transducer means thereafter generate a first output signal from said selected material reflection signals, which signal is representative of the thickness of the material. A second output signal, generated from the selected material outer surface reflection signal and the selected penetrant means tip reflection signal, is representative of the depth of penetration of said penetrant means. The first and second output signals are thereafter passed to said comparator means.

Failsafe means connected to the comparator means monitor said comparator means for a failsafe condition. If operation of the comparator means is interrupted because of loss of electrical power or if the driving means advance or retract the penetrant means, as measured by the output signal from the depth sensing means, faster or slower than an expected range of drive speeds for said driving means, a failsafe condition exists and the failsafe means cause withdrawal of the penetrant means from the material.

Figure 1:
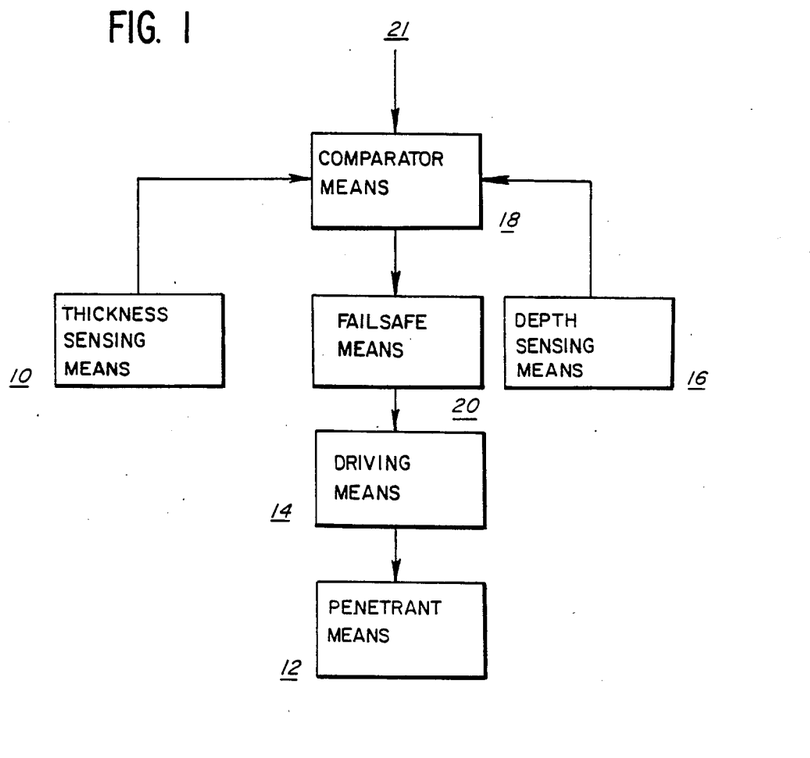
FIG. 1 is a block diagram showing the elements of the first embodiment of the controlled depth penetrant apparatus of this invention.

The preferred embodiments may also be more fully understood by reference to the drawings. Turning first to FIG. 1, there is shown a block diagram of the controlled depth penetrant apparatus. The controlled depth penetrant apparatus is electrically powered by known means which are not shown. Thickness sensing means 10 determine the thickness of the material to be penetrated at substantially the point of penetration. The measured thickness of the material, as determined by said thickness sensing means, is converted to a value proportional thereto which is generated as an output signal from said means 10.

Penetrant means 12 are used to penetrate the material of interest. Driving means 14 drive the penetrant means into said material or retract it therefrom. Depth sensing means 16 measure the depth of penetration of said penetrant means 12 into the material relative to the outer surface of the material. The measured depth of penetration of the penetrant means 12 is converted to a value proportional thereto which is generated as an output signal from said depth sensing means 16.

Comparator means 18 receive the output signal from the thickness sensing means 10 and receive the output signal from the depth sensing means 16.

An operator inputs to the comparator means 18 an input signal 21 comprising a signal representing a uniform thickness of material to be left unpenetrated adjacent to the inner surface, or a signal representing a uniform proportion of the thickness of the material at any point adjacent to the inner surface of the material to be left unpenetrated. If the signal computed by adding the input signal 21 representing a uniform thickness of material to be left unpenetrated adjacent to the inner surface to the output signal from the depth sensing means 16 is less than the output signal of the thickness sensing means 10, the driving means 14 are driven to automatically advance the penetrant means 12 inwardly with respect to the outer surface of the material until the computed signal and the output signal from the thickness sensing means 16 are equal. Similarly, if the computed signal is larger than the output signal from the thickness sensing means 16, the driving means 14 are driven to retract the penetrant means 12 outwardly with respect to the outer surface of the material until the computed signal and the output signal from the thickness sensing means are equal.

When the operator inputs to the comparator means 18 an input signal 21 comprising a signal representing a uniform proportion of the thickness of the material at any point adjacent to the inner surface thereof to be left unpenetrated, the comparator means 18 similarly controls the driving means 14 so that the penetrant means 12 penetrates to the proper depth. That is, if the signal computed by adding the input signal 21 representing a uniform proportion of the thickness of the material at any point adjacent to the inner surface thereof to be left unpenetrated to the output signal from the depth sensing means 16 is less than the output signal of the thickness sensing means 10, the driving means 14 are driven to automatically advance the penetrant means 12 inwardly with respect to the outer surface of the material until the computed signal and the output signal from the thickness sensing means are equal. Likewise, if the computed signal is larger than the output signal from the thickness sensing means 16, the driving means 14 are driven to retract the penetrant means 12 outwardly with respect to the outer surface of the material until the computed signal and the output from the thickness sensing means are equal.

Failsafe means 20 monitor the comparator means 18 for a failsafe condition. If operation of the comparator means 18 is interrupted, i.e., by an electrical power failure, or if the driving means 14 advance or retract the penetrant means 12, as measured by the output signal from the depth sensing means 16, faster or slower than an expected range of drive speeds for said driving means, a failsafe condition exists and the failsafe means 20 cause withdrawal of the penetrant means 12 from the material.

Figure 2:
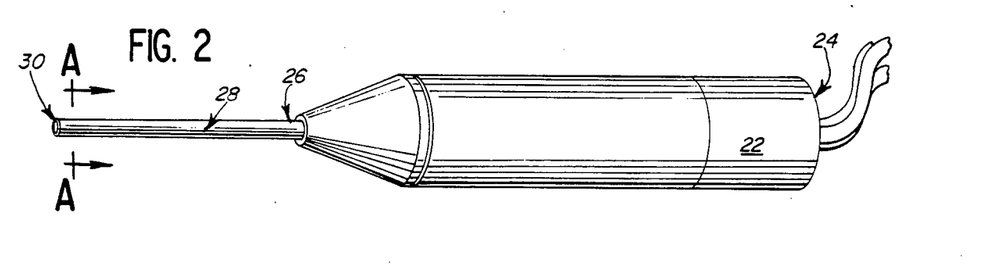
FIG. 2 is a perspective view of the hand-held portion of the controlled depth penetrant apparatus.

Turning to FIG. 2 there is shown a handle 22 of a preferred embodiment of the surgical instrument apparatus of the invention. The handle 22 has a first end 24 and a second end 26, and houses portions of the driving means, depth sensing means and thickness sensing means of the invention. An ultrasound transducer probe 28 is mounted in the second end 26 of the handle 22. The ultrasound transducer probe 28 is a portion of the ultrasound transducer means which comprise the thickness sensing means of this embodiment. The ultrasound transducer probe 28 shown in this embodiment is a hollow tube. A face 30 of the ultrasound transducer probe 28 is the portion of the ultrasound transducer means which is placed adjacent the outer surface of a material or tissue at substantially the point where the material or tissue is to be penetrated.

Figure 2A:
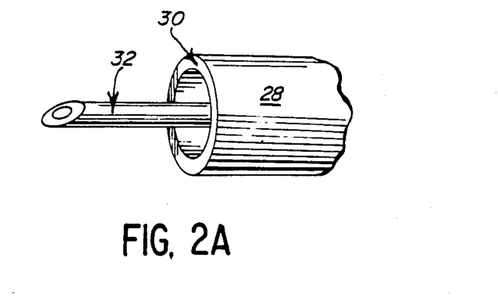
FIG. 2a is an enlarged partial cut away view taken at A—A of FIG. 2 showing the embodiment of a needle concentric with an ultrasound transducer in said apparatus.
Figure 2B:
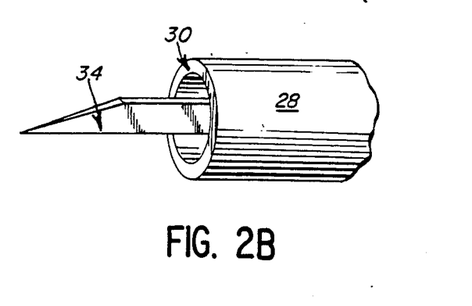
FIG. 2b is an enlarged partial cut away view taken at A—A of FIG. 2 showing the embodiment of a cutting blade concentric with an ultrasound transducer in said apparatus.

FIGS. 2a and 2b are alternative embodiments of the ultrasound transducer probe 28 showing an enlarged partial cut-away view taken at A—A of FIG. 2 of the face 30 of the ultrasound transducer probe 28 with the penetrant means visible. FIG. 2a shows a needle 32 concentric with the ultrasound transducer probe 28. FIG. 2b shows a cutting blade 34 concentric with the ultrasound transducer probe 28.

Placement of the needle 32 or the cutting blade 34 concentric with the ultrasound transducer probe 28 permits thickness measurement of the material adjacent to the face 30 at a point in closer proximity to the point of penetration of the needle 32 or the cutting blade 34 than if the needle 32 or the cutting blade 34 is placed just adjacent to the ultrasound transducer probe 28. The closer proximity of the point of thickness measurement to the point of penetration allowed by this concentric arrangement of the needle 32 or the cutting blade 34 and the ultrasound transducer probe 38 minimizes the slight uncertainty that is inherent when making a thickness measurement of a material at one point for purposes of approximating the thickness of the material at a given immediately adjacent point of penetration of a penetrant means.

Figures 3, 4:
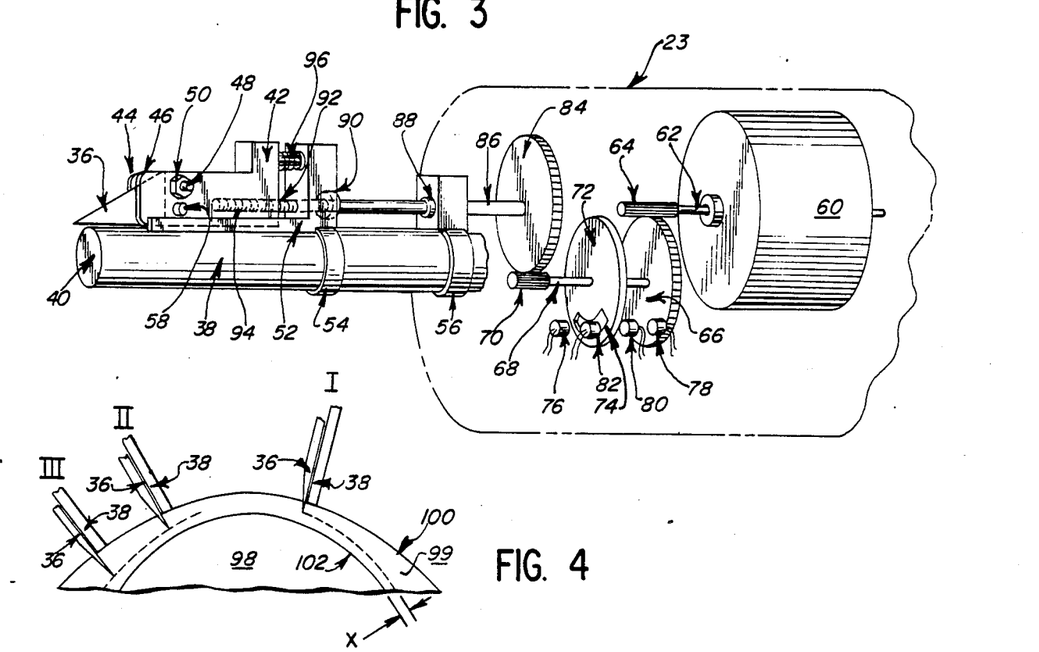
FIG. 3 is a perspective and cut-away view showing a second embodiment of the controlled depth penetrant apparatus of the invention with a cutting blade adjacent an ultrasound transducer and showing the arrangement of the motor driving means, speed reduction gear train and the photocell micrometer of said apparatus.
FIG. 4 is a partial cross section of an eye demonstrating the sequence of cutting positions for the cutting blade/ultrasound transducer probe arrangement of the controlled depth penetrant apparatus as it traverses the cornea during performance of a radial keratotomy.

FIG. 3 shows a cut-away perspective view of a portion of the preferred embodiment of the surgical instrument. The surgical instrument shown is particularly efficacious in performing a radial keratotomy on the eye of an animal. The handle 23 of the instrument is represented by a phantom outline. The preferred embodiment of the penetrant means is a cutting blade 36. Adjacent the cutting blade 36 is an ultrasound transducer probe 38 which comprises a portion of the thickness sensing means. The ultrasound transducer probe 38 has a face 40 which is placed in contact with the corneal outer surface in order to determine the thickness of the cornea between its outer and inner surfaces. A cutting blade holder 42 holds the cutting blade 36. The cutting blade 36 is placed between a first vise jaw 44 and a second vise jaw 46 on the cutting blade holder 42. A screw 48 passes through the first vise jaw 44 and the second vise jaw 46 on the cutting blade holder 42. A nut 50 tightens on the threaded end of the screw 48 to securely clamp the cutting blade between the first vise jaw 44 and the second vise jaw 46.

The cutting blade holder 42 is slidably mounted in a frame 52 that is securely fixed relative to the ultrasound transducer probe 38 by a first clamp 54 and a second clamp 56. A pin 58 passes through the cutting blade holder 42, and prevents rotational movement of the cutting blade holder 42.

A reversible D.C. motor 60 with an output shaft 62 is housed in the handle 23. A first gear 64 is fixed to the output shaft 62 of the reversible D.C. motor 60. A second gear 66 is attached to an input end of an intermediate shaft 68. A third gear 70 is attached to an output end of the intermediate shaft 68. A disk 72 is located on the intermediate shaft 68 between the second gear 66 and the third gear 70. The disk 72 has a slot 74 that is located towards its outer periphery. On one side of the disk 72 are located a light emitting diode 76 and a photocell 82. On the opposite side of the disk 72 are located a light emitting diode 78 and a photocell 80. The light emitting diode 76 is in substantial linear alignment with the photocell 80 while the light emitting diode 78 is in substantial linear alignment with the photocell 82, so that light from light emitting diode 76 will pass through the slot 74 and be detected by photocell 80, and light from light emitting diode 78 will pass through the slot 74 and be detected by photocell 82. The handle 23 provides an opaque housing and prevents room light from reaching photocells 80 and 82.

A fourth gear 84 is located on a driving shaft 86. The driving shaft 86 passes through a journal bearing 88 and a journal bearing 90 in frame 52. An end 92 of the shaft 86 is finely threaded. The cutting blade holder 42 has a hole 94 which is tapped to accommodate the finely threaded end 92 of the shaft 86. A pin and spring arrangement 96 is interspaced between the cutting blade holder 42 and the frame 52 in order to eliminate any play between the finely threaded end 92 of the output shaft 86 and the tapped hole 94.

As the reversible D.C. motor 60 is driven, it drives the output shaft 62. The first gear 64, securely pressed onto the output shaft 62, drives the second gear 66. Said second gear 66, the disk 72 and the third gear 70 are securely pressed onto the intermediate shaft 68, so that the first gear 64 drives the second gear 66 which in turn rotates the intermediate shaft 68, the disk 72 and the third gear 70. The fourth gear 84 is securely pressed onto shaft 86. Said third gear 70 drives the fourth gear 84 which in turn rotates the shaft 86. Rotation of the shaft 86 advances or retracts the tapped hole 94 onto the finely threaded end 92. Since the shaft 86 can only rotate and is fixed with respect to movement along its centerline, the cutting blade holder 42 and correspondingly the cutting blade 36 move linearly as a result of its rotation. The direction of the rotation of the output shaft 62 of the motor 60 determines whether the cutting blade 36 is advanced or retracted with respect to the end 40 of transducer 38, and hence with respect to the corneal surface.

While the intermediate shaft 68 is rotating, the disk 72 rotates at the same rate as said intermediate shaft. As the disk 72 is rotated the light beams between the light emitting diode 76 and the photocell 80 and between the light emitting diode 78 and the photocell 82 are passed through the slot 74. The light beams striking the photocells 80 and 82 become electrical pulses from the photocells 80 and 82. The electrical pulses from the photocells 80 and 82 are amplified by separate operational amplifiers to become strong digital pulses. The signals from both photocells are used to determine in which direction the disk 72 is rotating. The signal from one photocell is used to determine when the disk 72 has rotated a complete revolution. This combination of the disk 72 and the light emitting diodes 76 and 78 and the photocells 80 and 82 provide the counting portion of a photocell micrometer. In the preferred embodiment, the photocell micrometer is a portion of the depth sensing means.

As noted hereinbefore the preferred embodiment of the controlled depth penetrant apparatus of this invention is a surgical instrument for performing a radial keratotomy on the eye of an animal. The thickness sensing means thereof comprise ultrasound transducer means generally available in the art. The thickness of the cornea of said eye between its outer and inner surfaces is determined by generating a measuring signal by the ultrasound transducer unit coupled to the ultrasound transducer probe 38, and inwardly directing the measuring signal with respect to the outer corneal surface of the eye by placing the face 40 of the ultrasound transducer probe 38 in contact therewith. The ultrasound transducer probe 38 receives a plurality of reflected signals from the eye and then passes those signals to the ultrasound transducer unit. An operator can then select from the plurality of reflected signals those representing the corneal inner and outer surface reflections by utilizing discriminating means incorporated into the ultrasound transducer unit, which overall unit and probe means are generally available in the art.

The ultrasound transducer means then generate an output signal from the selected corneal reflection signals which is passed to a comparator means.

The penetrant means of the preferred embodiment are the cutting blade 36, which is used to incise the cornea as the instrument traverses the outer surface of the cornea. The driving means used to drive the cutting blade 36 comprise the following: The reversible D.C. motor 60 with the output shaft 62 driving the first gear 64; the first gear 64 driving the second gear 66, which is attached to and which drives the intermediate shaft 68; the third gear on the intermediate shaft drives the fourth gear 84 which in turn rotates shaft 86; the shaft 86, because of the finely threaded end 92, transmits its rotational movement into linear movement of the cutting blade holder 42, and consequently drives the cutting blade 36.

The depth sensing means of the preferred embodiment comprise the portion of the photocell micrometer shown in FIG. 3 plus amplification circuitry. Namely, in FIG. 3, when the disk 72 rotates, the slot 74 alternately allows passage of the light beam from the light emitting diode 76 to the photocell 80 and from the light emitting diode 78 to the photocell 82. The passage of the light beams periodically trigger the photocells 80 and 82. The electrical pulses from the photocells are amplified by separate operational amplifiers to become strong digital pulses. The signals from both photocells are used to determine in which direction the disk 72 is rotating, which indicates whether the cutting blade 36 is being advanced or retracted. The signal from one photocell is used to determine when the disk 72 has completed a revolution. The output from the operational amplifier, which indicates the completion of a revolution of the disk 72, is first counted in a preliminary counter of the comparator means which scales the pulses from the photocell so pulses leaving the preliminary counter are representative of the depth of penetration of the cutting blade 36.

The comparator means receive the output signal from the thickness sensing means and receive the output signal from the operational amplifiers of the depth sensing means. An operator inputs to the comparator means an input signal representing a uniform thickness of material to be left unpenetrated adjacent to the inner surface, or the operator adjusts the preliminary counter of the comparator means so that a uniform proportion of the thickness of the material at any point adjacent to the inner surface of the material is left unpenetrated. From the signals that the comparator means receive, advancement or retraction of the cutting blade 36 is effected.

The surgical instrument preferred embodiment of the controlled depth penetrant apparatus would accordingly function in an identical manner as described hereinbefore when the penetrant means are either a needle or a probe. The surgical instrument hence is useful in amniocentesis, as well as for performing venous puncture, arterial puncture, aspiration of a cyst or spinal taps.

FIG. 4 shows positions I, II and III of the preferred embodiment surgical instrument of the controlled depth penetrant apparatus during performance of a radial keratotomy procedure. The eye 98 of an animal and its cornea 99 with a corneal outer surface 100 and corneal inner surface 102, are generally shown. The three surgical instrument positions shown represent varying positions of the cutting blade 36 and the ultrasound transducer probe 38 as they near the anterior pole of the cornea 99. Position III shows the cutting blade 36 near the limbus of the cornea 99, and position II shows the cutting blade at a point on the cornea 99 intermediate that of positions I and III. The thickness "x" represents an unpenetrated portion of the cornea 99 adjacent to the corneal inner surface 102 which is of substantially uniform thickness. The positions I, II and III shown represent the relative movement of the cutting blade 36 and the ultrasound transducer probe 38 so as to leave the thickness "x" uncut.

Figure 5:
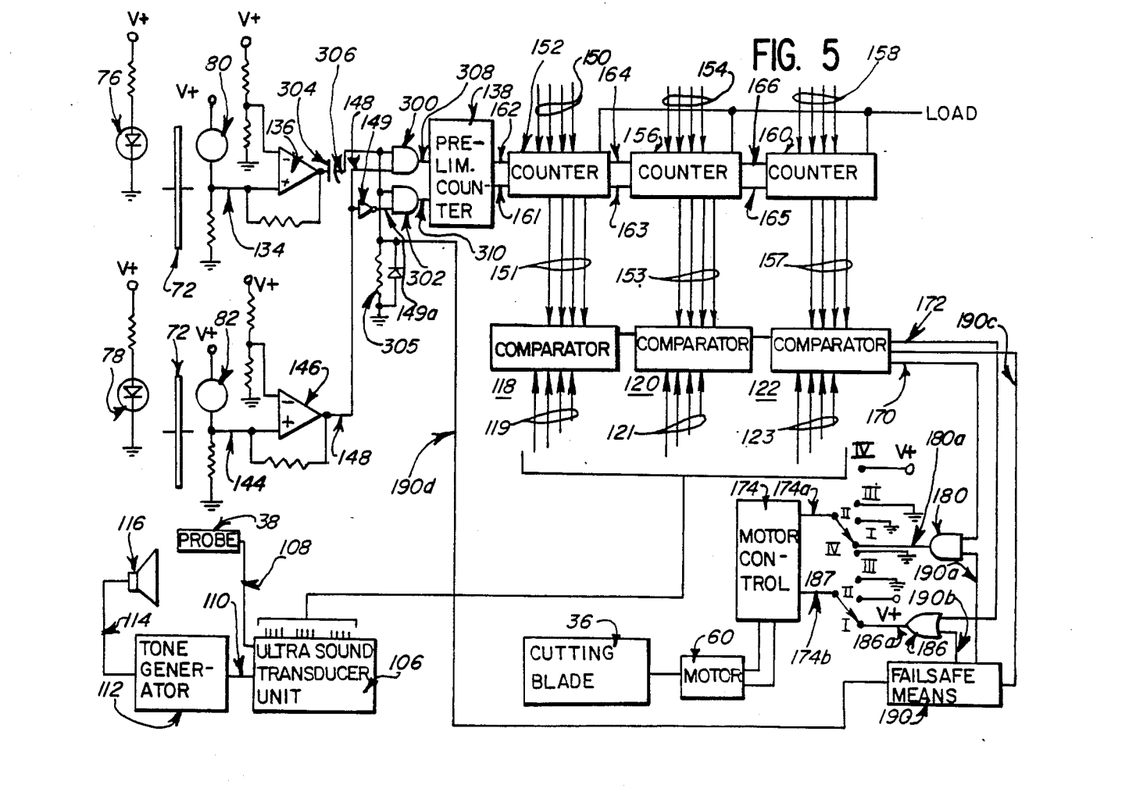
FIG. 5 is a combination block diagram and schematic circuit diagram of the second embodiment of the controlled depth penetrant apparatus of the invention.

FIG. 5 is a combination block diagram and schematic circuit diagram of the preferred embodiment of the controlled depth penetrant apparatus. As aforenoted, the operation of the apparatus of the preferred embodiment utilizes ultrasound transducer means as the thickness sensing means, which transducer means comprise an ultrasound transducer unit 106 and the ultrasound transducer probe 38. The ultrasound transducer probe 38 is placed in contact with the outer corneal surface of the eye. The ultrasound transducer unit 106 generates an ultrasound measuring signal which is passed to the ultrasound transducer probe 38 by conductor 108. Probe 38 directs the generated ultrasound measuring signal into the eye, from which a plurality of signals are generated as reflections of said measuring signal. These reflected signals are received by the probe 38 and conducted to the ultrasound transducer unit 106, by conductor 108.

For the most accurate determination of the corneal thickness, the ultrasound transducer probe 38 should be within approximately 10 degrees of perpendicular orientation to the cornea's outer surface tangent at the point that the thickness is to be determined. Deviation from perpendicular orientation of the ultrasound transducer probe 38 directs the ultrasound measuring signal and correspondingly the reflected signals through a greater thickness of the eye resulting in parallax, viz., misperception of distances between the underlying surfaces. Furthermore, the reflected signals from the underlying structures will be of decreased amplitude as the probe deviates from perpendicular orientation.

The reflected signals received by the ultrasound transducer unit 106 are passed to a tone generator 112 via conductor 110. The tone generator 112 produces an audio frequency signal the frequency of which increases, corresponding to greater deviations from perpendicular orientation of the probe and decreases corresponding to lesser deviations from perpendicular orientation. The audio frequency signal is conducted to a loudspeaker 116 to generate an audible tone. The operator adjusts the perpendicular orientation of the ultrasound transducer probe 38 in response to the frequency of the audible tone, adjustment being necessary whenever a relatively high frequency audio signal is heard.

From the plurality of reflected signals received by the ultrasound transducer unit 106, a discriminating means well known in the art and part of the ultrasound transducer unit 106 allows the operator to view a screen comprised within said transducer unit and select, from the plurality of reflected signals, those representing the corneal outer and inner surface reflections in a manner that allows the discriminating means to fix on those signals as the ultrasound transducer probe 38 traverses the corneal surface. From the discriminated signals representing the cornea's outer and inner surfaces the thickness sensing means generate a binary coded decimal number signal which corresponds to the distance between the corneal outer and inner surfaces. The binary coded decimal number signal representative of corneal thickness is input into three binary coded decimal magnitude comparators 118, 120 and 122.

The magnitude comparators 118, 120 and 122 are interconnected or ganged so that they function as a unit, namely, the magnitude comparing output of comparator 118 is connected to the magnitude comparing input of comparator 120, the magnitude comparing output of comparator 120 is connected to the magnitude comparing input of comparator 122. The comparator 118 receives the "one's" output of the binary coded decimal number signal from the ultrasound transducer unit 106 via conductors 119. The comparator 120 receives the "ten's" output of the binary coded decimal number signal from the ultrasound transducer unit 106 via conductors 121. The comparator 122 receives the "hundred's" output of the binary coded decimal number signal from the ultrasound transducer unit 106 via conductors 123.

While the ultrasound transducer unit 106 measures the thickness of the cornea, the cutting blade 36 is penetrating the cornea. The cutting blade 36 is advanced or retracted through a slide and gear reduction arrangement driven by the motor 60. The slotted rotating disk 72 forms part of the gear reduction arrangement. First light emitting diode 76 is located on one side of the disk 72 and first photocell 80 is located on the opposite side of the disk 72.

The first light emitting diode 76 and the first photocell 80 form the counting portion of the photocell micrometer. The first light emitting diode 76 and the first photocell 80 are in substantial linear alignment so that the light from the first light emitting diode 76 passes through the slot 74 of the disk 72 and reaches the first photocell 80. As the disk 76 rotates and allows the light beam to pass to the first photocell 80, it generates an electrical pulse signal. For each complete revolution of the disk 72, the photocell 76 generates one pulse signal. The pulse signals are transmitted to an operational amplifier 136 via conductor 134, which amplifies them and generates a positive pulse signal.

The second light emitting diode 78 is located on one side of the disk 72, and the second photocell 82 is located on the opposite side of the disk 72. The second light emitting diode 78 and the second photocell 82 are in substantial linear alignment so that the light from the second light emitting diode 78 passes through the slot 74 of the disk 72 and reaches the second photocell 82. The second light emitting diode 78 and the second photocell 82 in combination with the first light emitting diode 76 and the first photocell 80 form the portion of the photocell micrometer which determines the direction of rotation of the disk 72, which is also indicative of whether the cutting blade 36 is advancing or retracting. The disk 72 rotates and allows the light beam to pass to the second photocell 82, which generates an electrical pulse signal for each complete rotation of the disk 72. The pulses are transmitted to an operational amplifier 146, via conductor 144, which amplifies them and generates a positive pulse signal.

The positive output pulse signal from the operational amplifier 146 is of a time duration equal to the time duration that the light strikes the second photocell 82 and is passed through conductor 148 to an inverter 149 and to a first input on an "AND" gate 300. The output pulse signal of the inverter 149 passes through a conductor 149a to a first input on an "AND" gate 302. The positive output pulse signal from the operational amplifier 136 is of a time duration equal to the time duration that the light strikes the first photocell 80 and is passed through a capacitor 304 to a conductor 306 which thereafter conducts it to a second input on "AND" gate 300 and to a second input on "AND" gate 302.

The result of the passing of the pulse signal from the operational amplifier 136 through the capacitor 304 is that said pulse signal decays to zero volts with a time constant equal to the product of the capacitance of capacitor 304 and the resistance of a resistor 305 such that said time constant is less than the time interval between the pulse signal generated by the operational amplifier 136 and the pulse signal generated by the operational amplifier 146, namely the time interval between the pulsing of photocells 80 and 82. The capacitor 304 insures that when the operational amplifier 136 is the first operational amplifier to emit a pulse that pulse signal decays before the occurrence of the pulse from the operational amplifier 146.

The sequence of the pulsing of the photocell 80 and the photocell 82 corresponds to either an advance or retraction of the cutting blade 36. When the sequence of pulsing corresponds to an advance of the cutting blade 36, a preliminary counter 138 is enabled to up count. The pulse signal which passes through the conductor 148 is at positive source voltage prior to the pulse signal from operational amplifier 136 which passes through capacitor 304 to conductor 306. The inverter 149 inverts said pulse signal to zero volts so that the first input to "AND" gate 302 via conductor 149a is zero volts. The first input to the "AND" gate 300 via conductor 148 is at positive source voltage. Thus the "AND" gate 300 is enabled and the "AND" gate 302 is disabled. The pulse signal from the capacitor 304 passing through conductor 306 to the second input of the "AND" gate 300 occurs during the time interval of the pulse signal that passes through conductor 148 to the first input of the "AND" gate 300, said "AND" gate 300 thereafter generates a signal which passes through conductor 308 to the increment terminal of the preliminary counter 138. This signal causes a stored count in the preliminary counter to increase by one. The "AND" gate 302 does not generate a signal since the first input to "AND" gate 302 via conductor 149a is zero volts.

When the sequence of pulsing signals corresponds to a retraction of the cutting blade 36, the preliminary counter 138 is enabled to down count. The pulse from the operational amplifier 136 which passes through capacitor 304 to conductor 306 occurs prior to the pulse signal from the operational amplifier 146 and has decayed to zero volts before the operational amplifier 146 pulses a signal since the time constant is less than the time interval between the pulse signal generated by the operational amplifier 136 and the pulse signal generated by the operational amplifier 146.

The pulse signal passing through conductor 306 passes to the second input of "AND" gate 300 and the second input of "AND" gate 302. However, since the first input to "AND" gate 300 via conductor 148 is zero volts because the photocell 82 has not begun to pulse the "AND" gate 300 does not generate a signal. The invertor 149 inverts the zero voltage of conductor 148 to a positive source voltage signal which is passed via conductor 149a to the first input of "AND" gate 302. The "AND" gate 302 in turn generates a decrement signal which is passed through conductor 310 to the decrement terminal of the preliminary counter 138. The decrement signal causes a stored count in the preliminary counter to decrease by one.

The preliminary counter 138 passes a signal via conductor 162 to increment "one's" counter 152 when the counter 138 is incrementing and it reaches its greatest count and resets to zero. The "one's" counter 152 passes a signal via conductor 164 to increment "ten's" counter 156 when the counter 152 is incrementing and it reaches its greatest count and resets to zero. Likewise, the "ten's" counter 156 passes a signal via conductor 156 to increment "hundred's" counter 160 when the counter 156 is incrementing and it reaches its greatest count and resets to zero.

The preliminary counter 138 passes a signal via conductor 161 to decrement "one's" counter 152 when the counter 138 is decrementing and reaches zero and resets to its greatest count. The "one's" counter 152 passes a signal via conductor 163 to decrement "ten's" counter 156 when the counter 152 is decrementing and it reaches zero and resets to its greatest count. Likewise, the "ten's" counter 156 passes a signal via conductor 165 to decrement "hundred's" counter 160 when the counter 156 is decrementing and it reaches zero and resets to its greatest count.

When the thickness of material unpenetrated adjacent the inner surface of the cornea is a uniform proportion of the material thickness, the preliminary counter 138 divides the counted pulses by an appropriate dividing factor which proportionally increases the counted pulses of the preliminary counter so that the signal from the preliminary counter 138 is representative of an increased proportion of the depth the cutting blade 36 has advanced or retracted. Otherwise, the pulse signals counted by the preliminary counter 138 and the signal from the preliminary counter 138 are directly representative of the depth the cutting blade 36 has advanced or retracted.

A signal representing a selected uniform unpenetrated thickness of cornea to be left adjacent the inner surface of the cornea is passed to the "one's" counter 152, the "ten's" counter 156, and the "hundred's" counter 160 at an input 168 via conductors 150, 154 and 158 respectively before the cutting blade begins to penetrate the cornea and simulates an initial fictitious penetration equal to the thickness of the cornea to be left unpenetrated adjacent the inner surface.

The counted pulse signals from the "one's" counter 152 are passed to the "one's" comparator 118 via conductors 151. The counted pulse signals from the "ten's" counter 156 are passed to the "ten's" comparator 120 via conductors 153. And, the counted pulse signals from the "hundred's" counter 160 are passed to the "hundred's" comparator 122 via conductors 157. The ganged comparators 118, 120 and 122 compare the signals passed via conductors 151, 153 and 157, representing the depth of penetration of the cutting blade 36 plus the unpenetrated thickness of cornea to be left adjacent the inner surface of the cornea and the signals passed via conductors 119, 121 and 123 representing the thickness of the cornea between the outer surface and the inner surface. The ganged comparators 118, 120 and 122 determine if the input signals are equal or which signal is larger.

A motor control 174 controls the driving of motor 60 allowing either advance or retraction of the cutting blade 36. A double pole four position switch 187 has four positions indicated by I, II, III and IV. Position I allows automatic operation of the motor control 174 and the motor 60 as will subsequently be described. The motor control 174 controls the motor 60 to retract the cutting blade 36 if the switch is manually operated to position II. A corresponding motor control signal passes through conductor 174b to the first terminal on motor control 174.

When the switch 187 is manually operated to position III, no signal passes to motor control 174, consequently, the motor 60 is not driven and the cutting blade 36 is neither advanced nor retracted. When the switch is manually operated to position IV, a signal passes through conductor 174a to the second terminal on the motor control 174 to operate the motor 60 and advance the cutting blade 36.

Under normal circuit operation, an advance enable signal from a failsafe means 190 passes through conductor 190a to enable the "AND" gate 180. With the switch 187 in position I automatic operation of the motor control occurs. When the signals from the ultrasound transducer unit 106 are greater than the signals from the counters 152, 156 and 160, an output signal passes through conductor 170 to a first input of an "AND" gate 180. These combined signals generate an output signal from "AND" gate 180 which signal passes through conductor 180a, when the switch 187 is in position I, and through conductor 174a on to motor control 174 to control the motor 60 so that the cutting blade 36 is advanced.

When the signals from the ultrasound transducer unit 106 are less than the signals from the counters 152, 156 and 160, an output signal passes through conductor 172 to a first input of an "OR" gate 186. The signal generates an output signal from "OR" gate 186 which signal passes through conductor 186a and through conductor 174b on motor control 174 to control the motor 60 so that the cutting blade is retracted.

When the signals from the ultrasound transducer unit 106 are equal to the signals from the counters 152, 156 and 160, an output signal passes through conductor 190c to the failsafe means 190.

Figure 6:
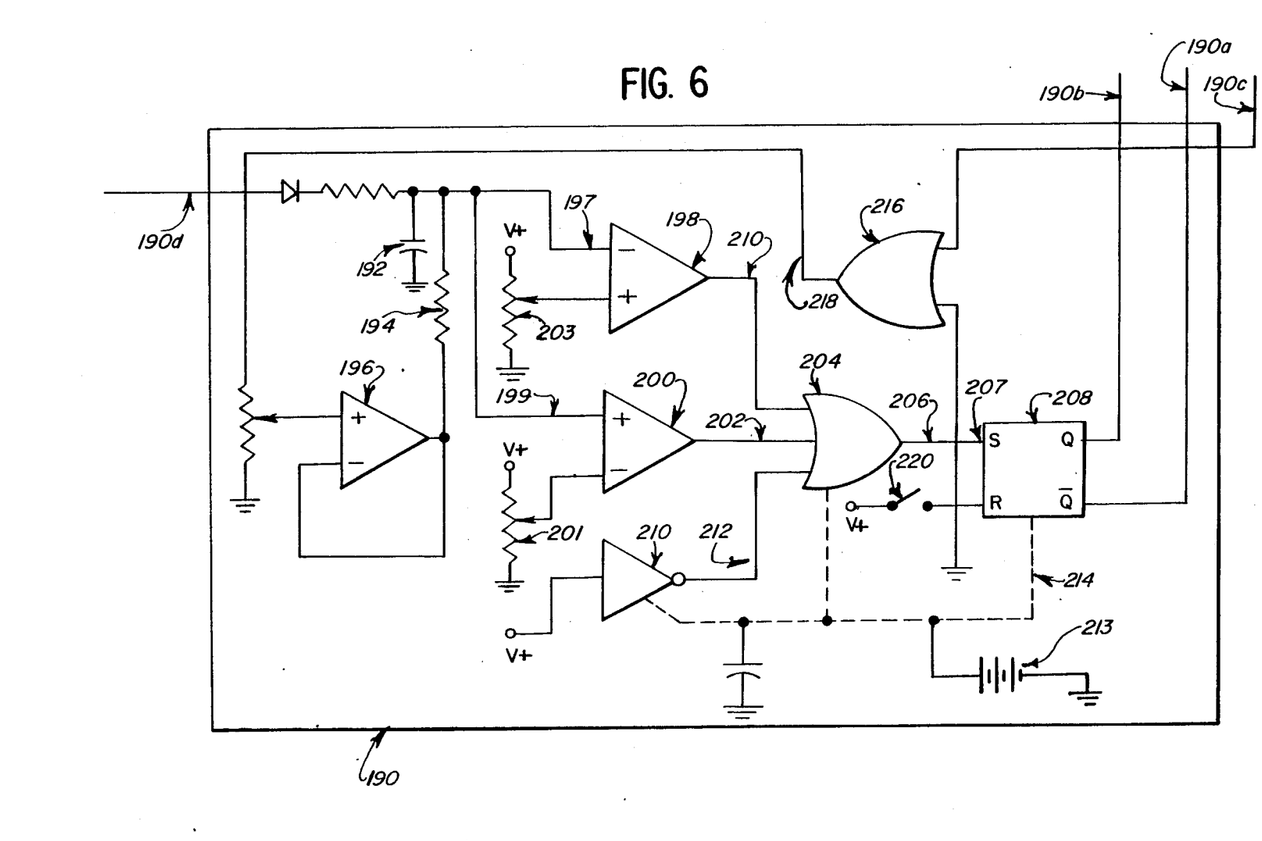
FIG. 6 is a schematic circuit diagram of the failsafe means of the second embodiment of the controlled depth penetrant apparatus of the invention.

FIG. 6 is a schematic circuit diagram of the failsafe means 190. A conductor 190d inputs a pulse signal to the failsafe means 190 which pulse signal is the same pulse signal that is input to the preliminary counter 138. The pulse signal on conductor 190d charges a capacitor 192 at a rate substantially proportional to the rate the pulse signals are input to preliminary counter 138. A resistor 194 discharges the capacitor 192 such that the voltage on the capacitor 192 is proportional to the rate of pulse signals reaching the preliminary counter 138. The resistor 194 discharges the capacitor 192 through the output of an operational amplifier 196 when the circuit is in normal operation and the cutting blade 36 is being advanced or retracted.

Operational amplifiers 198 and 200 detect the voltage on the capacitor 192 via conductors 197 and 199 respectively. When the voltage on the capacitor 192 is greater than a maximum threshold voltage which maximum threshold voltage is manually set in the illustrated embodiment by adjusting a variable resistor 201 to correspond to a maximum safe permissible pulse signal rate, the operational amplifier 200 passes a signal via conductor 202 to a first input on "OR" gate 204. Thereafter, an output signal from "OR" gate 204 passes via conductor 206 to a "set" terminal 207 on a set-reset type flip-flop 208. The uncomplimented "Q" output of flip-flop 208 passes a signal to conductor 190b which signal is input to "OR" gate 186 (FIG. 5) to thereafter pass through conductor 186a to the motor control 174 such that the motor 60 retracts the cutting blade 36. The complimented "$\overline{Q}$" output of flip-flop 208 removes the usually present advance enable signal from conductor 190a so that no signal is input to the second input of "AND" gate 180 and "AND" gate 180 passes no signal on. The maximum safe permissible pulse signal rate is determined by the maximum speed that the disk 72 (FIG. 5) will rotate dictated by the maximum loaded speed of the motor 60 by accounting for minimal frictional losses incurred in advancing or retracting the cutting blade 36 (FIG. 5) in the softest cornea.

When the voltage on the capacitor 192 is less than a minimum threshold voltage which minimum threshold voltage is manually set in the illustrated embodiment by adjusting a variable resistor 203 to correspond to a minimum safe permissible pulse signal rate, the operational amplifier 198 passes a signal via conductor 210 to a second input of "OR" gate 204. Thereafter an output signal from "OR" gate 204 passes via conductor 206 to the "set" terminal 207 of the flip-flop 208. The uncomplimented "Q" output of flip-flop 208 passes a signal to conductor 190b which signal is input into "OR" gate 186 (FIG. 5) to thereafter pass through conductor 186a to the motor control 184 such that the motor 60 retracts the cutting blade 36. The complimented "$\overline{Q}$" output of flip-flop 208 removes the usually present advance enable signal from conductor 190a so that no signal is input to the second input of "AND" gate 180 and "AND" gate 180 passes no signal on. The minimum safe permissible pulse signal rate is determined by the minimum speed that the disk 72 (FIG. 5) will rotate dictated by the minimum loaded speed of the motor 60 by advancing or retracting the cutting blade 36 (FIG. 5) in the hardest cornea.

When the voltage on the capacitor 192 is between said maximum and said minimum threshold voltages no signals are output from operational amplifiers 198 or 200. The failsafe circuit remains in a safe state so that normal operation continues and the complimented output of flip-flop 208 passes the advance enable signal via conductor 190a to the second input of "AND" gate 180 (FIG. 5) so that when a signal is input to the first input gate 180 via conductor 170, "AND" gate 180 will thereafter pass a signal.

When there is an interruption to the electrical power supply of this embodiment, an invertor 210 having an input conductor which is connected to positive supply voltage passes a signal via conductor 212 to the "OR" gate 204 which functions to control the retraction of the cutting blade 36 as previously described.

The power supply to invertor 210, "OR" gate 204 and flip-flop 208 is derived from a protected power source 213 via protected power conductor 214, independent from the electrical power supply to the apparatus of the invention.

When the signals from the ultrasound transducer unit 106 (FIG. 5) are equal to the signals from the counters 152, 156 and 160, an output signal passes through conductor 190c to the failsafe means 190. The signal passed to the failsafe means 190 via conductor 190c passes the signal to an "OR" gate 216 which thereafter passes a signal via conductor 218 to the operational amplifier 196 so that the capacitor 192 does not discharge when the cutting blade 36 is at the desired depth.

A reset switch 220 resets the flip-flop 208 and applies a proper initial charge to capacitor 192.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and the scope of the invention.

We claim as our invention:

1. Apparatus for penetrating a material which has an outer surface and an inner surface, whereby said material is penetrated inwardly from said outer surface while leaving adjacent to said inner surface an unpenetrated portion thereof, comprising:

penetrant means for penetrating said material;

driving means connected to said penetrant means for advancing or retracting said penetrant means relative to the outer surface of said material;

depth sensing means for determining the depth of penetration of said penetrant means into said material relative to said outer surface and generating a signal proportional thereto;

thickness sensing means for determining the thickness of said material between the outer and inner surfaces of said material at a point directly adjacent to said thickness sensing means, which thickness sensing means determine the thickness of said material at substantially the point of penetration of said penetrant means and generate a signal proportional thereto, and;

comparator means connected to said depth sensing means, thickness sensing means, and driving means, which compare said signal proportional to the depth of penetration of said penetrant means into said material relative to said outer surface to an input signal proportional to the desired unpenetrated thickness adjacent to the inner surface of said material and to said signal proportional to the thickness of said material at substantially the point of penetration of said penetrant means, said point serving substantially as a common reference point for said depth sensing means and said thickness sensing means which comparator means thereafter provide an output signal which controls said driving means so that the penetration of said penetrant means inwardly from the outer surface of said material is adjusted so as to leave unpenetrated a portion of said material adjacent the inner surface.

2. The apparatus of claim 1 wherein said comparator means provide an output signal whereby the penetration of said penetrant means is adjusted such that the unpenetrated portion of said material adjacent to said inner surface is of substantially uniform thickness.

3. The apparatus of claim 1 wherein said comparator means provide an output signal whereby the penetration of said penetrant means is adjusted such that the unpenetrated portion of said material at any point adjacent to said inner surface is a substantially uniform proportion of the thickness of said material at said point.

4. The apparatus of claim 1 wherein said penetrant means are a cutting blade.

5. The apparatus of claim 1 wherein said penetrant means are a needle.

6. The apparatus of claim 1 wherein said penetrant means are a probe.

7. The apparatus of claims 1, 2, 3, 4, 5 or 6 wherein said thickness sensing means comprise ultrasound transducer means whereby the thickness of said material between the outer and inner surfaces thereof is determined by generating a measuring signal by said transducer means, inwardly directing said signal with respect to said outer surface of said material, thereafter receiving a plurality of reflected signals from said material with said transducer means, selecting from said signals those representing the material inner and outer surface reflections by utilizing discriminating means comprised within said transducer means, and generating an output signal from said selected material reflection signals, which signal is representative of said thickness.

8. The apparatus of claim 7 wherein said depth sensing means are a photocell micrometer.

9. The apparatus of claim 7 wherein said depth sensing means are a variable resistor vernier.

10. The apparatus of claims 1, 2, 3, 4, 5 or 6 wherein an ultrasound transducer means comprise both said thickness sensing means and said depth sensing means, whereby the thickness of said material between the outer and inner surfaces thereof, and the depth of penetration of said penetrant means into said material relative to said outer surface, are determined by generating a measuring signal by said transducer means, inwardly directing said signal with respect to said outer surface of said material, thereafter receiving a plurality of reflected signals from said material with said transducer means, selecting from said signals those representing the material inner and outer surface reflections and the penetrant means tip reflection by utilizing discriminating means comprised within said transducer means, and generating a first output signal from said selected material reflection signals, which signal is representative of said thickness, and a second output signal from said selected material outer surface reflection signal and said selected penetrant means tip reflection signal, which signal is representative of said depth.

11. The apparatus of claims 1, 2, 3, 4, 5 or 6 wherein said depth sensing means are a photocell micrometer.

12. The apparatus of claims 1, 2, 3, 4, 5 or 6 wherein said depth sensing means are a variable resistor vernier.

13. A surgical instrument for performing a radial keratotomy on the eye of an animal, whereby the cornea of said eye is penetrated inwardly from its outer surface while leaving adjacent to its inner surface an unpenetrated portion thereof, comprising:

a cutting blade for penetrating said cornea;

driving means connected to said cutting blade for advancing or retracting said cutting blade relative to the outer surface of said cornea;

depth sensing means for determining the depth of penetration of said cutting blade into said cornea relative to said outer surface and generating a signal proportional thereto;

thickness sensing means for determining the thickness of said cornea between the outer and inner surfaces of said cornea at a point directly adjacent to said thickness sensing means, which thickness sensing means determine the thickness of said cornea at substantially the point of penetration of said cutting blade and generate a signal proportional thereto, and;

comparator means connected to said depth sensing means, thickness sensing means, and driving means, which compare said signal proportional to the depth of penetration of said cutting blade into said cornea relative to said outer surface to an input signal proportional to the desired unpenetrated thickness adjacent to the inner surface of said cornea and to said signal proportional to the thickness of said cornea at substantially the point of penetration of said penetrant means, said point serving substantially as a common reference point for said depth sensing means and said thickness sensing means which comparator means thereafter provide an output signal which controls said driving means so that the penetration of said cutting blade inwardly from the outer surface of said cornea is adjusted so as to leave unpenetrated a portion of said cornea adjacent the inner surface.

14. The surgical instrument of claim 13 wherein said comparator means provide an output signal whereby the penetration of said cutting blade is adjusted such that the unpenetrated portion of said cornea adjacent to said inner surface is of substantially uniform thickness.

15. The surgical instrument of claim 13 wherein said comparator means provide an output signal whereby the penetration of said cutting blade means is adjusted such that the unpenetrated portion of said cornea at any point adjacent to said inner surface is a substantially uniform proportion of the thickness of said cornea at said point.

16. The surgical instrument of claims 13, 5 or 6 wherein said thickness sensing means comprise ultrasound transducer means whereby the thickness of said cornea between the outer and inner surfaces thereof is determined by generating a measuring signal by said transducer means, inwardly directing said signal with respect to said outer surface of said eye, thereafter receiving a plurality of reflected signals from said eye with said transducer means, selecting from said signals those representing the corneal inner and outer surface reflections by utilizing discriminating means comprised within said transducer means and generating an output signal from said selected corneal reflection signals, which signal is representative of said thickness.

17. The surgical instrument of claim 16 wherein said depth sensing means are a photocell micrometer.

18. The surgical instrument of claim 17 further comprising failsafe means connected to said comparator means to effect withdrawal of said cutting blade from the interior of said cornea on existence of a failsafe condition.

19. The surgical instrument of claim 16 wherein said depth sensing means are a variable resistor vernier.

20. The surgical instrument of claims 13, 5 or 6 wherein said thickness sensing means comprise light transducer means whereby the thickness of said cornea between the outer and inner surfaces thereof is determined by generating a plurality of light measuring signals by said transducer means, inwardly directing said signals with respect to said outer surface of said eye, thereafter receiving a plurality of reflected signals from said eye with said transducer means representing the corneal inner surface reflections, and generating an output signal from said corneal reflection signals, which signal is representative of said thickness.

21. The surgical instrument of claim 20 wherein said depth sensing means are a photocell micrometer.

22. The surgical instrument of claim 21 further comprising failsafe means connected to said comparator means to effect withdrawal of said cutting blade from the interior of said cornea on existence of a failsafe condition.

23. The surgical instrument of claim 20 wherein said depth sensing means are a variable resistor vernier.

24. The surgical instrument of claims 13, 14 or 15 wherein an ultrasound transducer means comprise both said thickness sensing means and said depth sensing means, whereby the thickness of said cornea between the outer and inner surface thereof, and the depth of penetration of said cutting blade into said cornea relative to said outer surface, are determined by generating a measuring signal by said transducer means, inwardly directing said signal with respect to said outer surface of said eye, thereafter receiving a plurality of reflected signals from said eye with said transducer means, selecting from said signals those representing the corneal inner and outer surface reflections and the cutting blade tip reflection by utilizing discriminating means comprised within said transducer means, and generating a first output signal from said selected corneal reflection signals, which signal is representative of said thickness, and a second output signal from said selected corneal outer surface reflection signal and said selected cutting blade tip reflection signal, which signal is representative of said depth.

25. The surgical instrument of claim 24 further comprising failsafe means connected to said comparator means to effect withdrawal of said cutting blade from the interior of said cornea on existence of a failsafe condition.

26. The surgical instrument of claims 13, 14 or 15 wherein said depth sensing means are a photocell micrometer.

27. The surgical instrument of claims 13, 14, or 15 wherein said depth sensing means are a variable resistor vernier.

28. The surgical instrument of claims 13, 14 or 15 further comprising failsafe means connected to said comparator means to effect withdrawal of said cutting blade from the interior of said cornea on existence of a failsafe condition.

29. A method of penetrating a material having an outer surface and a substantially inaccessible inner surface with penetrant means, wherein said penetration is effected inwardly from said outer surface while leaving adjacent to said inner surface an unpenetrated portion of said material, comprising the steps of:

determining the thickness of said material between the outer and inner surfaces thereof by thickness sensing means at a point directly adjacent to said thickness sensing means, said point being substantially the point of intended penetration of said penetrant means, and generating a signal proportional thereto;

penetrating said material with said penetrant means;

advancing or retracting said penetrant means relative to the outer surface of said material by driving means connected thereto;

determining the depth of penetration of said penetrant means into said material relative to said outer surface thereof by depth sensing means and generating a signal proportional thereto, and;

comparing said signal proportional to the depth of penetration of said penetrant means into said material relative to said outer surface thereof to an input signal proportional to the desired unpenetrated thickness adjacent to the inner surface of said material and to said signal proportional to the thickness of said material at substantially the point of penetration of said penetrant means said point serving substantially as a common reference point for said depth sensing means and said thickness sensing means by comparator means, and thereafter controlling said driving means so that the penetration of said penetrant means inwardly from the outer surface of said material is adjusted so as to leave unpenetrated a portion of said material adjacent the inner surface.

30. The method of claim 29 wherein said comparator means provide an output signal whereby the penetration of said penetrant means are adjusted such that the unpenetrated portion of said material adjacent to said inner surface is of substantially uniform thickness.

31. The method of claim 29 wherein said comparator means provide an output signal whereby the penetration of said penetrant means is adjusted such that the unpenetrated portion of said material at a point adjacent to said inner surface is a substantially uniform proportion of the thickness of said material at said point.

32. A surgical method for performing a radial keratotomy on the eye of an animal wherein the cornea of said eye is penetrated inwardly from its outer surface with a cutting blade while leaving adjacent to its inner surface an unpenetrated portion of said cornea and a plurality of incisions are made which incisions radiate from the anterior pole to the limbus of said cornea, said incisions being effected by the steps of:

determining the thickness of said cornea between the outer and inner surfaces thereof by thickness sensing means at a point directly adjacent to said thickness sensing means, said point being substantially the point of intended penetration of said cutting blade and generating a signal proportional thereto;

penetrating said cornea with said cutting blade;

advancing or retracting said cutting blade relative to the outer surface of said cornea by driving means connected thereto;

determining the depth of penetration of said cutting blade into said cornea relative to said outer surface thereof by depth sensing means and generating a signal proportional thereto, and;

comparing said signal proportional to the depth of penetration of said cutting blade into said cornea relative to said outer surface thereof to an input signal proportional to the desired unpenetrated thickness adjacent to the inner surface of said cornea and to said signal proportional to the thickness of said material at substantially the point of penetration of said cutting blade said point serving substantially as a common reference point for said depth sensing means and said thickness sensing means by comparator means, and thereafter controlling said driving means so that the penetration of said cutting blade inwardly from the outer surface of said cornea is adjusted so as to leave unpenetrated a portion of said cornea adjacent the inner surface.

33. The method of claim 32 wherein said comparator means provide an output signal whereby the penetration of said cutting blade is adjusted such that the unpenetrated portion of said cornea adjacent to said inner surface is of substantially uniform thickness.

34. The method of claim 32 wherein said comparator means provide an output signal whereby the penetration of said cutting blade is adjusted such that the unpenetrated portion of said cornea at a point adjacent to said inner surface is a substantially uniform proportion of the thickness of said cornea at said point.

* * * * *